US010330631B2

(12) United States Patent
Blick et al.

(10) Patent No.: US 10,330,631 B2
(45) Date of Patent: Jun. 25, 2019

(54) HIGH-SPEED DNA SEQUENCING WITH OPTICALLY ACTIVE NANOPORE

(71) Applicant: Wisconsin Alumni Research Foundation, Madison, WI (US)

(72) Inventors: Robert H. Blick, Hamburg (DE); Paul H. Gwozdz, Hamburg (DE); Abhishek Bhat, Madison, WI (US); Wolfgang Hansen, Hamburg (DE); Christian Heyn, Lueneburg (DE)

(73) Assignee: Wisconsin Alumni Research Foundation, Madison, WI (US)

( * ) Notice: Subject to any disclaimer, the term of this patent is extended or adjusted under 35 U.S.C. 154(b) by 563 days.

(21) Appl. No.: 14/815,228

(22) Filed: Jul. 31, 2015

(65) Prior Publication Data
US 2017/0029882 A1  Feb. 2, 2017

(51) Int. Cl.
| G01N 27/327 | (2006.01) |
| C12Q 1/6869 | (2018.01) |
| G01N 21/64 | (2006.01) |
| G01N 33/487 | (2006.01) |
| G01N 30/88 | (2006.01) |
| B82Y 15/00 | (2011.01) |

(52) U.S. Cl.
CPC ....... *G01N 27/3278* (2013.01); *C12Q 1/6869* (2013.01); *G01N 21/6408* (2013.01); *G01N 33/48721* (2013.01); *B82Y 15/00* (2013.01); *G01N 21/6489* (2013.01); *G01N 2030/8827* (2013.01)

(58) Field of Classification Search
CPC ............ C12Q 1/6869; C12Q 2565/631; C12Q 2565/113; C12Q 2565/155; G01N 33/48721
See application file for complete search history.

(56) References Cited

U.S. PATENT DOCUMENTS

| 2005/0019784 A1* | 1/2005 | Su ................... C12Q 1/6869 435/6.12 |
| 2009/0015351 A1 | 1/2009 | Qin et al. |
| 2010/0129603 A1 | 5/2010 | Blick et al. |
| 2011/0111179 A1 | 5/2011 | Blick et al. |
| 2012/0141729 A1 | 6/2012 | Blick et al. |

(Continued)

OTHER PUBLICATIONS

Heyn et al.; "Scaling of the structural characteristics of nanoholes created by local droplet etching." Journal of Applied Physics 115, No. 2 (2014): pp. 024309-1 thru 024309-7; Germany.

(Continued)

*Primary Examiner* — J. Christopher Ball
(74) *Attorney, Agent, or Firm* — Boyle Fredrickson, S.C.

(57) ABSTRACT

A nanoscale-sized pore positioned between two reservoirs may sequence biomolecules by detecting changes in the emitted light due to a change in charge of portions of the biomolecules as they pass through the pore such as affect an emission frequency of a quantum structure proximate to the pore opening. The nanopores may be fabricated using local droplet etching whose randomness is accommodated by lowering the droplet density to permit isolation of nanopores in tiles that may be adhered to an underlying supporting substrate having an aligned opening. The nanopore-tiles may be integrated with commonly applied glass chips and may be employed in microfluidic circuitry.

20 Claims, 3 Drawing Sheets

(56) References Cited

U.S. PATENT DOCUMENTS

| | | |
|---|---|---|
| 2013/0098762 A1 | 4/2013 | Blick |
| 2013/0249530 A1 | 9/2013 | Blick et al. |
| 2014/0087474 A1* | 3/2014 | Huber .................. C12Q 1/6869 |
| | | 436/94 |
| 2014/0253153 A1 | 9/2014 | Blick et al. |
| 2014/0266147 A1 | 9/2014 | Blick et al. |

OTHER PUBLICATIONS

Stemmann et al.; "Local droplet etching of nanoholes and rings on GaAs and AlGaAs surfaces." Applied Physics Letters 93. No. 12 (2008). pp. 123108-1 thru 123108-3; Germany.

* cited by examiner

HIGH-SPEED DNA SEQUENCING WITH OPTICALLY ACTIVE NANOPORE

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to a system for the direct sequencing of polymers such as DNA and RNA by passing the polymer through a nanoscale pore and measuring a light signal modulated by the polymer.

Genetic information is encoded in a molecule of deoxyribonucleic acid (DNA) as a sequence of nucleotides: guanine, adenine, thymine, and cytosine. Discovering the sequence of these nucleotides in DNA and other similar molecules is a foundational technology in biological studies.

One promising method of sequencing is "nanopore sequencing" in which a single strand of DNA, forming half of the DNA helix, is passed through a nanoscale opening in a membrane between two reservoirs. This nanopore opening may, for example, be a protein channel held in a lipid bilayer. An electrical potential or other gradient (i.e. molar concentrations. thermal, etc.) may be applied across the reservoirs to produce an ion flow between the reservoirs pulling the strand of DNA through the nanopore. As the strand passes through the nanopore, it modulates the ion current through the nanopore as a function of the size of the nucleotide obstructing the nanopore. This alteration in the ion current may then be analyzed to determine the nucleotide sequence. An example system of nanopore sequencing is described in PCT patent WO/2008102120 entitled: "Lipid Bilayer Sensor System", and in European patent 2695949 entitled: "Nucleic Acid-based Nano Pores or Transmembrane Channels and their Uses", both hereby incorporated by reference.

The electrical signals produced by changes in ion current through a nanopore with different nucleotides are very small in amplitude and accordingly long sampling times are required to distinguish the signals from noise, resulting in a slowing down of the sequencing process. The ability to obtain required sampling times may not be available because of the high speed of motion of the DNA strand through the nanopore.

SUMMARY OF THE INVENTION

The present invention provides a sequencing apparatus using an optically active nanopore. The nanopore includes a semiconductor nanoscale structure near the pore opening exhibiting quantum confinement effects that are affected by the electrical field of the long chain molecule passing through. Field-induced changes in the band gap of the nanoscale structure, as different portions of the long chain molecule pass through the nanopore, cause the emission of light at different frequencies such as may be mapped to different structures of the long chain molecule.

More specifically, one embodiment the invention provides an apparatus for a measurement of biomolecules using a separator with a nanopore providing a passage through the separator, the nanopore incorporating a nanoscale semiconductor element proximate to the passage that is adapted to emit light with a frequency dependent on a charge of a portion of biomolecules passing through the nanopore. A reservoir system holds a fluid on opposite sides of the separator to provide a flow of biomolecules through the nanopore from one side of the separator to the other and a spectrometer receives emitted light from the nanoscale semiconductor element to measure frequency of that light as biomolecules flow through the nanopore. An electronic computer communicates with the spectrometer and executes a program to relate light frequency measured by the spectrometer to structure of the portion of the biomolecules thereby providing a sequencing of biomolecule structures as the biomolecules passes through the nanopore.

It is thus a feature of at least one embodiment of the invention to provide an improved (high-speed) sensing structure for sequencing biomolecules making use of local interaction between the biomolecule and a light-emitting quantum confinement structure.

The nanoscale semiconductor element may be a ring concentric with the nanopore and bounded by different materials on nanoscale dimensions to provide a structure exhibiting quantum confinement effects.

It is thus a feature of at least one embodiment of the invention to provide a "quantum ring" sensor that may maximize sensitivity of the quantum structure to the electrical field of a material within the ring.

The different materials bounding the ring may also be semiconducting materials potentially increasing the sensitivity of the detection mechanism.

It is thus a feature of at least one embodiment of the invention to provide a quantum structure that may be readily fabricated using integrated circuit techniques on semiconductor materials.

The nanoscale semiconductor element and different materials may be group III/V semiconductors but can also be group II/VI.

It is thus a feature of at least one embodiment of the invention to provide materials that may produce a light output more easily communicated from the nanopore to a measuring instrument.

The semiconductor may be selected from the group consisting of: gallium arsenide, aluminum gallium arsenide, and indium arsenide.

It is thus a feature of at least one embodiment of the invention to provide a nanoscale semiconducting structure employing well-characterized materials.

The apparatus may further include a light source for providing stimulating energy to the nanoscale semiconductor element to promote an emission of light from the nanoscale semiconductor element.

It is thus a feature of at least one embodiment of the invention to promote light emission by providing a source of stimulating energy that may be tailored to the hand gap of the nanoscale semiconductor element.

The separator may be a solid material substantially unbroken outside of the nanopore over an area contacting fluid of the reservoir structure.

It is thus a feature of at least one embodiment of the invention to eliminate the need for fragile lipid bilayers normally used as separators between reservoirs in favor of a substantially continuous and more robust solid-state separator.

The separator may be a membrane holding the nanopore and adhered to a substrate of different material, the substrate having an aperture aligned with the nanopore.

It is thus a feature of at least one embodiment of the invention to permit fabrication of separators with nanopores using techniques, such as a local droplet etching, which have limited working depth by attaching a thin membrane etched using these techniques to a thicker substrate while aligning an opening in the two.

The nanopore may be substantially circular or may be non-circular in cross-section, either sized to control an orientation of the biomolecule as it passes through the nanopore, It is thus a feature of at least one embodiment of the invention to promote the sequencing of biomolecules by mechanically constraining the flow of biomolecules through the nanopore.

The invention also provides a method of manufacturing separators of the type that can isolate reservoirs of liquid across at least one optically active nanopore. In the method, a matrix material is fabricated on a sacrificial layer supported by a first substrate and subjected to local droplet etching in which metal droplets erode nanoscale holes through the matrix material to the sacrificial layer. A second substrate is then prepared with a plurality of apertures larger than the nanoscale holes, wherein the second substrate is thicker than the matrix material. The matrix material is then removed from the sacrificial layer and adhered to the second substrate so that at least one nanopore aligns with at least one aperture. The adhered matrix material and second substrate are then divided into multiple separator elements each including a continuous passage through a nanoscale hole and aperture.

It is thus a feature of at least one embodiment of the invention to provide a robust separator that can eliminate the need for bilayer lipid membranes and yet still provide nanoscale holes.

The method may include separating the matrix material into a plurality of tiles after the local droplet etching and independently attaching the tiles to the second supporting substrate.

It is thus a feature of at least one embodiment of the invention to accommodate the random distribution of nanoscale holes obtained by techniques such as local droplet etching.

The matrix material may be adhered to the second substrate by van-der-Waals forces.

It is thus a feature of at least one embodiment of the invention to provide a method of attaching the matrix material to a supporting structure that permits a period of adjustment before permanently affixing the matrix material to the supporting structure.

The method may include the step of coating the nanoscale hole with a semiconductor material different from a material of the walls of the nanoscale hole.

It is thus a feature of at least one embodiment of the invention to permit the construction of a quantum confinement element proximate to a nanoscale opening for use in sequencing biomolecules and other similar applications.

These particular features and advantages may apply to only some embodiments falling within the claims and thus do not define the scope of the invention.

DETAILED DESCRIPTION OF THE PREFERRED EMBODIMENT

Figure 1:
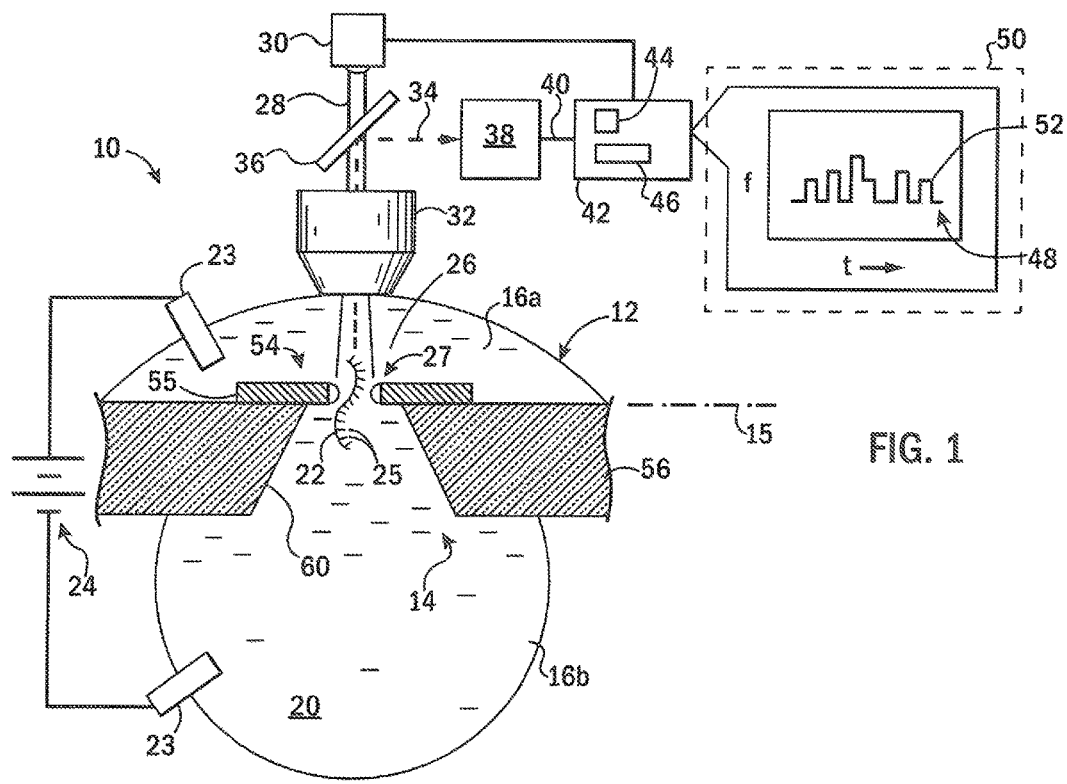
FIG. 1 is a block diagram of a sequencing apparatus employing an optically active nanopore in exaggerated scale as positioned in a separator between reservoirs of fluid.

Referring now to FIG. 1, an apparatus 10 for characterizing molecules passing through a nanopore may comprise a generally rigid planar separator 12 extending along a plane 15 and having an opening 14 passing through the separator 12 generally perpendicular to the plane 15.

A reservoir structure having first and second reservoirs 16a and 16b may be constructed on either side of the separator 12 about the opening 14 to be separated from each other by the separator 12 and communicating only through the opening 14. These reservoirs 16a and 16b may be filled with a conductive fluid 20 such as a buffer solution, for example, KCl solution, as held by capillary attraction or a fluidic channel. Reservoir 16a may have an introduced source of biomolecules 22 (for example, single DNA strands or double strand DNA helices and the necessary proteins and enzymes to separate the helix into strands) suspended therein.

Each of the reservoirs 16a and 16b may hold electrodes 23 (for example, silver/silver chloride electrodes) communicating between with the liquid of the reservoir structure and a voltage source 24 together to provide an electrical voltage across the opening 14 tending to produce an ionic flow from reservoir 16a to reservoir 16b. This flow may draw the biomolecules 22 along with it causing individual biomolecules 22 to thread through the opening 14. As monomers 25 of the biomolecules 22 pass through the opening 14, different electrical charges associated with each monomer 25 may influence a quantum structure 27 proximate to the opening 14.

In particular, during the flow of the biomolecules 22, the quantum structure 27 may be excited with a light beam 28, for example, from ultraviolet light source 30 focusing a beam of ultraviolet light on the quantum structure 27, for example, through microscope objective 32. In response to this excitation, the quantum structure 27 will emit light 34 which may pass upward through the microscope objective 32 along the path of the light beam 28 and then be separated by a beam splitter 36 from the light beam 28 and then directed toward a spectrometer 38. As will be discussed below, the frequency of this emitted light 34 will be affected by electrical charges associated with different monomers 25 of the biomolecules 22 as they pass through the nanopore 26 generating a unique fingerprint for each monomer 25 related to the light frequency.

The spectrometer 38 receiving the frequency modulated emitted light 34 provides a frequency output 40 indicating a center frequency of the emitted light 34. This frequency output 40 is then received by an electronic computer 42 for analysis. As is generally understood in the art, the electronic computer 42 may include one or more processing elements 44 communicating with a memory 46 holding a stored program executable on the processing elements 44 to analyze the frequency output 40. The computer 42 may also control the light source 30 both to turn it on and off and optionally to adjust its intensity and/or frequency to improve the signal-to-noise ratio of the measured emitted light 34.

The computer 42 executing a stored program will in turn provide sequence information 48, for example, presented on an electronic display 50 or the like, providing a time sequence 52 of measurements indicating the sequence of monomers 25 in the biomolecules 22 as a function of time thereby sequencing the biomolecules 22. In the case of a DNA biomolecule 22, the monomers 25 will be guanine, adenine, thymine and cytosine whose different electrical fields provide different frequency modulation of the emitted light 34.

In one embodiment, the separator 12 holding the nanopore 26 through which the biomolecules 22 pass, may be a laminated structure, for example, including a tile 54 of a semiconductor matrix material 55 holding the actual nanopore 26 supported on a support substrate 56 having a larger aperture 60 having diameters from 1 to 10 micrometers.

The tile 54 of semiconductor matrix material 55 may be of relatively small area, for example, several tens of microns on each side of a square perimeter and may have a thickness between 20 and 400 nanometers. Tile 54 will be relatively flexible and in some manufacturing processes may include multiple nanopores 26 and for this reason is supported on the upper face of the larger support substrate 56, for example, the latter constructed of borosilicate glass quartz of much greater thickness (measured perpendicularly to plane 15), for example, in a range from 0.1 millimeters to 1.2 millimeters or more.

As noted, the nanopore 26 will be aligned with the larger aperture 60 in the support substrate 56, the latter such as may be fabricated using a laser according the technique described in U.S. Pat. No. 8,092,739 "Retro-Percussive Technique For Creating Nanoscale Holes" and U.S. Pat. No. 8,623,496 "Laser Drilling Technique for Creating Nanoscale Holes" assigned to the assignee of the present invention and hereby incorporated by reference. In this technique, an ultraviolet absorbent liquid is confined to the back-side of a quartz substrate to absorb energy when pulsed by an excimer laser passing through the substrate.

Figure 2:
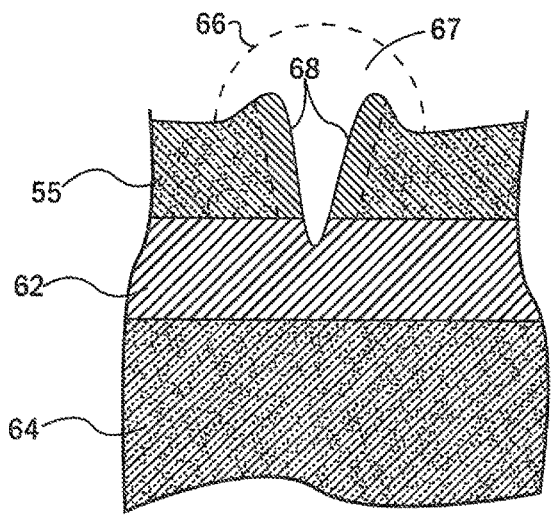
FIG. 2 is a detailed cross-section of the nanopore of FIG. 1 during fabrication, showing a semiconductor matrix material supported on a sacrificial layer attached to a construction substrate immediately after being etched by local droplet etching.

Referring now to FIG. 2, the nanopore 26 may be formed in the matrix material 55 by means of local droplet etching (LDE) of the type described in "Local droplet etching of nanoholes and rings on GaAs and Al GaAs surfaces", A. Steinmann, Ch. Heyn, T. Köppenl, T. Kipp and W. Hansen Appl. Phys. Lett. 93, 123108 (2008) and "Scaling of the structural characteristics of nanoholes created by local droplet etching", Ch. Heyn, S. Schnüll and W. Hansen, J. Appl. Phys. 115, 024309 (2014), hereby incorporated by reference, In this process, the matrix material 55, for example, an aluminum gallium arsenide semiconductor, may be fabricated on a sacrificial layer 62, for example, of silicon dioxide or aluminum arsenide, this sacrificial layer 62 in turn supported by a much thicker and substantially rigid fabrication substrate 64, for example, a silicon wafer. Sacrificial layer 62 is selectively removable by a solvent such as hydrofluoric acid so as to permit release of the matrix material 55 from the fabrication substrate 64 without damage to the matrix material 55, While the matrix material 55 is held on the fabrication substrate 64 by the sacrificial layer 62, metal droplets 66 are then formed on its surface through a nucleation process described in the above-cited references. In one embodiment these metal droplets 66 may be gallium or indium. During a post-growth thermal annealing step, the droplets 66 create nanopits 67 into the matrix material 55. While the inventors do not wish to be bound by a particular theory, it is believed that the central process for this etching is a diffusion of arsenic from the matrix material 55 into the metal droplet and subsequent droplet material removal.

The resulting nanopit 67 extends through the matrix material 55 into the sacrificial layer 62 and becomes a nanopore 26 when the sacrificial layer 62 is removed. When the droplet 66 is gallium on an aluminum gallium arsenide matrix material 55, the inner walls 68 of the nanopore 26 will be predominantly gallium arsenide in contrast to the aluminum gallium arsenide of the matrix material 55. When the droplet 66 is indium, the material of the inner walls 68 will be indium arsenide. This technique may also be used with a gallium arsenide matrix material 55 in which ease the material of the inner wall 68 may be gallium arsenide with a different material property than the matrix material 55 caused by higher amounts of gallium, or indium arsenide, The average diameter of the nanopore 26 will be less than 1000 nanometers.

Figure 3:
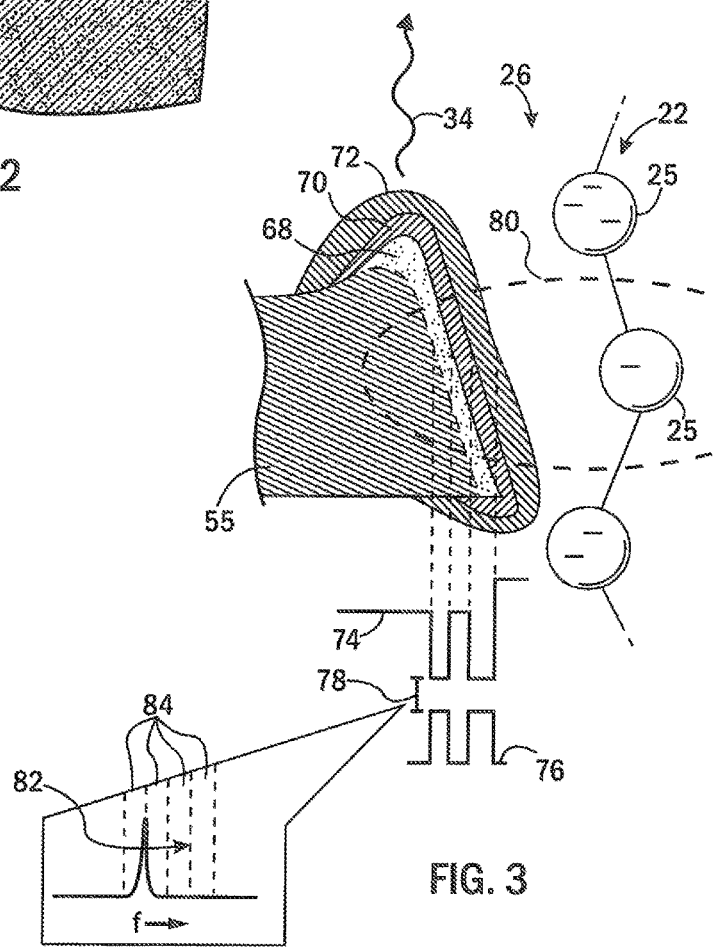
FIG. 3 is an expanded cross-section of the nanopore during use showing additional layers applied to the opening of the nanopore to create a quantum structure having conduction and valence bands providing a bandgap that varies with electrical interaction between the quantum structure and a proximal molecule being analyzed, and further showing in an inset, a spectrum of emitted light such as varies with such electrical interaction.

Referring now to FIG. 3, this inner wall 68 may be covered with a coating 70 of aluminum gallium arsenide (in the case of an aluminum gallium arsenide matrix material 55) to sandwich the inner wall 68 between two dissimilar semiconducting materials of aluminum gallium arsenide. The thickness of the inner wall 68 measured in the plane 15 may be less than 10 nanometers to provide quantum structure 27 having quantum confinement effects as will be discussed and as are caused by the confining effects of the coating 70 and material of the matrix material 55, In addition a capping layer 72, for example, gallium arsenide may be placed over the coating 70. Generally gallium arsenide is compatible with DNA and thus a suitable capping material for capping layer 72; however, other materials may be used to provide a nonreactive outer surface with different biomolecules 22.

The semiconductor materials of matrix material 55, inner walls 68, and coating 70 including capping layer 72 create a set of adjacent conduction bands 74 and valence bands 76 of different energies that produce a quantum confinement in the inner walls 68 as bounded by inner walls 68 and capping layer 72 as is necessary for optical emissions. This bounding of the inner wall 68 provides quantum structure 27.

Generally the semiconductor materials may be selected from group III/V or group II/VI, however other material such as strained silicon germanium may be used. The group MN materials may be selected from gallium arsenide, aluminum gallium arsenide, and indium arsenide.

A bandgap 78 between the conduction bands 74 and valence band 76 of the inner walls 68 define a bandgap energy which determines the frequency of light emitted from the inner wall 68 when electrons drop between the conduction bands 74 and valence band 76. The value of this bandgap energy separating the valence and conduction bands 76 and 74 of the inner wall 68 will change slightly in response to the electric field 80 associated with monomers 25 of the biomolecule 22 proximate to the inner walls 68. The result will be a change in the frequency 82 of emitted light 34 depending on the monomer 25.

This change in emitted light frequency 82 is detected by the spectrometer 38 shown in FIG. 1 and a measurement of center frequency transmitted to the computer 42. A program running on the computer 42 may employ a predetermined a set of frequency zones 84 which are empirically determined and then used in mapping frequency of emitted light 34 to different zones 84 associated with different monomers 25. Accordingly, movement of the frequency 82 of the emitted light 34 among the zones 84 provides a characterization of the monomers 25 and hence a sequencing of the biomolecule 22 as it passes through the nanopore 26.

Figure 4:
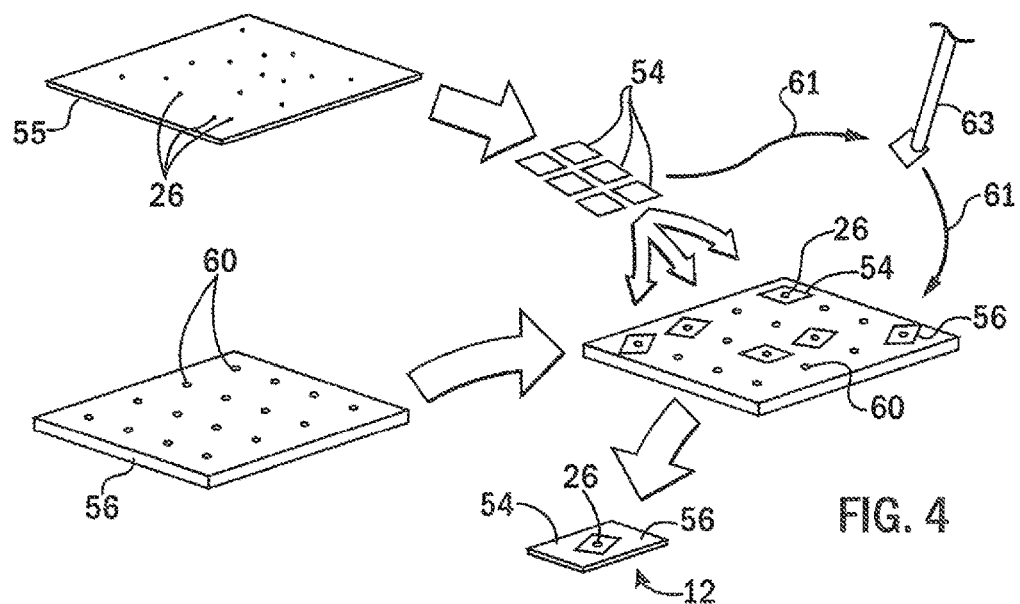
FIG. 4 is a simplified flowchart showing the formation of a separator of FIG. 1 by the attachment of nanopores in a matrix material to the supporting substrate.

Referring now to FIG. 4, fabrication of the separators 12 is complicated by the largely random process of nucleation used in local droplet etching. Accordingly the present invention, in one embodiment, controls the local droplet etching to reduce the density of holes produced to be, for example, an average one nanopore 26 for every tile 54 (for example, one nanopore 26 for every 10 to 100 micrometer square). As will be discussed below, multiple nanopores 26 may be accommodated on an individual tile 54. Separation of the matrix material 55 into the tiles for may be accomplished by defining on the matrix material 55 a grid using optical lithography to provide an etch mask for a dry etch along boundaries between the tiles 54. Finally a selective wet edge step may be carried out so that the tiles 54 released float off the carrier surface.

The support substrate 56 is then prepared with the regular spacing of larger apertures 60 and the separated tiles 54 placed on the support substrate 56 so that the nanopores 26 align with larger apertures 60 with the tiles 54. Adjustment of the tiles 54 on the support substrate 56 may be accomplished while the tiles 54 are wet and may float on a liquid layer held by capillary force between the tile 54 and the support substrate 56. Once properly located, the tile 54 is firmly attached to the support substrate 56 by van-der-Waals forces, which come into play when the liquid layer between the tile 54 and the support substrate 56 evaporates.

Alternatively dry tiles 54 may be placed directly on the support substrate 56 with suction enabled micro-pipettes 63 aligning the dry tiles 54 with the larger apertures 60 per arrows 61.

The support substrate 56 may then be cut into the final dimension of the separators 12 as described above, each separator 12 holding one tile 54 and providing one functioning nanopore 26. It will be appreciated that each tile 54 may have multiple nanopores 26 and that the alignment of a single nanopore 26 with a single larger aperture 60 may serve to limit the number of channels passing through each separator 12.

In one embodiment, the WE etched matrix material 55 may be bonded directly to the support substrate 56 without being separated into tiles 54 with the expectation that the randomly located nanopores 26 will randomly align with some of the larger apertures 60. These locations of alignment may then be determined, for example, by observation using photoluminescence measurements or the like and used to guide the division of the matrix material 55 and support substrate 56 into the separators 12.

It is contemplated that in some embodiments, separators 12 with multiple nanopores 26 aligned with larger aperture 60 may be provided to be used for parallel sequencing operations where multiple biomolecules 22 are sequenced in parallel using separate light collectors and separate spectrographic analysis.

Figure 5:
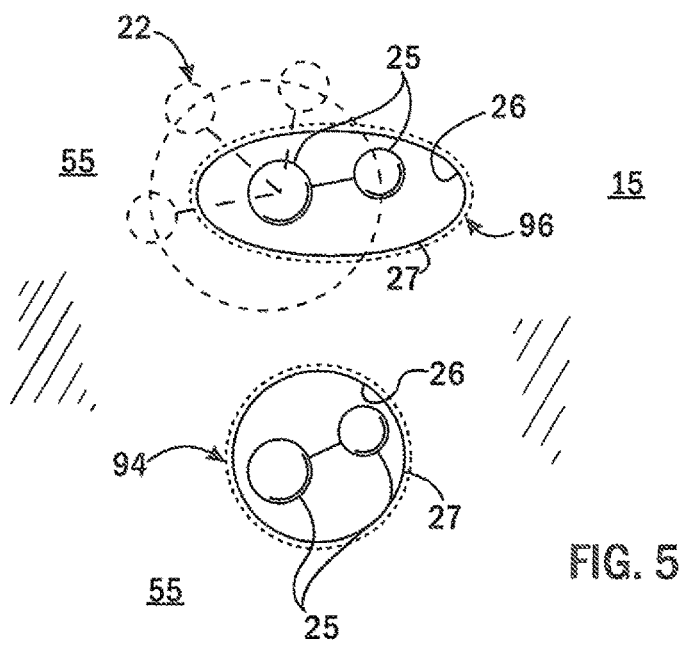
FIG. 5 is a top plan depiction of an elliptical and circular nanopore such as may be created with the present invention.

Referring now to FIG. 5, it will be appreciated that the nanopore 26 may have a circular opening 94 (seen along the viewing axis normal to the plane 15) or by taking advantage of anisotropic characteristics of the semiconductor matrix material 55, for example, crystal axis directions, which may have an ellipsoidal opening 96. This latter shape may be desirable for sequencing of bio-molecules that are not circular in cross-section. For example, this opening 96 may be sized to roughly conform to a lateral extension of the monomers 25 in the plane 15 thereby provoking a rotation of the biomolecule 22 as it passes through the nanopore 26 such as may assist in controlling the progression of the biomolecule 22 through the nanopore 26 Or to select among different biomolecules, Alternatively this orientation may assist in providing more standardized effects of the electrostatic field of the monomers 25 On the surrounding quantum structure 27 formed from inner wall 68.

In this document, "different materials" refers to materials having different band energies and includes materials with different doping concentrations such as may be suitable for creating a quantum confinement structure.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and Words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a "processor" or "processor unit" should generally be understood to refer broadly to general-purpose computer processing elements for executing stored programs (software) comprised of sequences of arithmetic and logical operations stored in the general-purpose memory. The term "circuit" as used herein should be considered to broadly include both analog and digital circuitry together with associated firmware. The term "program" generally refers to a sequence of operations executed by a processor or circuit. References to memory, unless otherwise specified, can combinations of different memory structures including solid-state and electromechanical memories and may describe a distributed system of main memory and multiple cache layers.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An apparatus for a measurement of biomolecules comprising:

a separator having a nanopore providing a passage through the separator, the nanopore incorporating a nanoscale semiconductor element proximate and fixed with respect to the passage and adapted to emit light, such light as emitted from the nanoscale semiconductor element having a frequency dependent on a charge of a portion of a biomolecule passing through the nanopore, the nanoscale semiconductor element providing physical structure producing a quantum confinement of electrons dropping between a conduction band and valence band to change a frequency of the light emitted by those electrons as a function of field induced interaction with the biomolecules;

a reservoir system holding a fluid on opposite sides of the separator to provide a flow of biomolecules through the nanopore from one side of the separator to the other;

a spectrometer receiving emitted light from the nanoscale semiconductor element to measure frequency of that light with flow of biomolecules through the nanopore; and an electronic computer communicating with the spectrometer and executing a program to relate light frequency measured by the spectrometer to the structure of the portion of the biomolecules thereby providing a sequencing of a biomolecule structure as it passes through the nanopore.

2. The apparatus of claim 1 wherein the nanoscale semiconductor element is a donut concentric with the nanopore and bounded by different materials on nanoscale dimensions to provide a structure exhibiting quantum confinement effects.

3. The apparatus of claim 2 wherein the different materials are semiconductor materials.

4. The apparatus of claim 3 wherein the nanoscale semiconductor element and different materials are selected from group III/V semiconductors; group II/V semiconductors, and strained silicon and/or germanium.

5. The apparatus of claim 4 wherein the group III/V semiconductors are selected from the group consisting of gallium arsenide, aluminum gallium arsenide, and indium arsenide.

6. The apparatus of claim 1 wherein the separator is a solid material substantially unbroken outside of the nanopore over an area contacting fluid of the reservoir structure.

7. The apparatus of claim 1 wherein the separator is a membrane holding the nanopore and adhered to a substrate of different material, the substrate having an aperture aligned with the nanopore.

8. The apparatus of claim 1 wherein the reservoir system includes electrodes communicating with reservoir fluids to provide for an ionic flow from one side of the separator to the other.

9. The apparatus of claim 1 wherein the nanopore is substantially circular in cross-section.

10. The apparatus of claim 1 wherein the nanopore is noncircular in cross-section and sized to control an orientation of the biomolecules that are non-circular in cross-section as they pass through the nanopore.

11. The apparatus of claim 1 including an output device providing a human readable output indicating a sequence of the biomolecules.

12. An apparatus for a measurement of biomolecules comprising:

a separator having a nanopore providing a passage through the separator, the nanopore incorporating a nanoscale semiconductor element proximate to the passage and adapted to emit light with a frequency dependent on a charge of a portion of a biomolecule passing through the nanopore;

a reservoir system holding a fluid on opposite sides of the separator to provide a flow of biomolecules through the nanopore from one side of the separator to the other;

a spectrometer receiving emitted light from the nanoscale semiconductor element to measure frequency of that light with flow of biomolecules through the nanopore; and an electronic computer communicating with the spectrometer and executing a program to relate light frequency measured by the spectrometer to the structure of the portion of the biomolecules thereby providing a sequencing of a biomolecule structure as it passes through the nanopore;

wherein the nanoscale semiconductor element is a donut concentric with the nanopore and hounded by different materials on nanoscale dimensions to provide a structure exhibiting quantum confinement effects; and wherein the nanopore has a dimension of less than 1000 nanometers and wherein the doughnut extends less than 10 nanometers inward from the nanopore passage measured in a plane normal to an axis of the nanopore through the separator.

13. An apparatus for a measurement of biomolecules comprising:

a separator having a nanopore providing a passage through the separator, the nanopore incorporating a nanoscale semiconductor element proximate to the passage and adapted to emit light with a frequency dependent on a charge of a portion of a biomolecule passing through the nanopore;

a reservoir system holding a fluid on opposite sides of the separator to provide a flow of biomolecules through the nanopore from one side of the separator to the other;

a spectrometer receiving emitted light from the nanoscale semiconductor element to measure frequency of that light with flow of biomolecules through the nanopore; and an electronic computer communicating with the spectrometer and executing a program to relate light frequency measured by the spectrometer to the structure of the portion of the biomolecules thereby providing a sequencing of a biomolecule structure as it passes through the nanopore;

further including a light source for providing stimulating energy to the nanoscale semiconductor element to promote an emission of light from the nanoscale semiconductor element.

14. A method for characterizing biomolecules comprising the steps of:

(a) passing the biomolecules from a first to a second reservoir through a nanopore providing a nanoscale semiconductor element proximate and fixed with respect and to the nanopore to emit light, such light, as emitted from the nanoscale semiconductor element, having a frequency dependent on a charge of a portion of a biomolecule passing through the nanopore, the nanoscale semiconductor element having structure providing quantum confinement of electrons dropping between a conduction band and valence band to change a frequency of the light emitted by those electrons as a function of field induced interaction with the biomolecules;

(b) during a transit of the biomolecules through the nanopore, applying a stimulating energy to the nanoscale semiconductor element to promote an emission of light therefrom;
(c) measuring a frequency of emitted light; and
(d) relating the frequency of emitted light over time to a sequence of structures of the biomolecules passing through the nanopore to provide a sequencing of the biomolecules.

15. A method of manufacturing separators for isolating reservoirs of liquid across at least one optically active nanopore, the method comprising the steps of:
 (A) fabricating a matrix material on a sacrificial layer supported by a first substrate;
 (B) subjecting the matrix material to local droplet etching in which metal droplets erode nanoscale holes through the matrix material to the sacrificial layer;
 (C) preparing a second substrate with a plurality of apertures larger than the nanoscale holes, wherein the second substrate is thicker than the matrix material;
 (D) removing the matrix material from the sacrificial layer and adhering it to the second substrate so that at least one nanopore aligns with at least one aperture; and
 (E) dividing the adhered matrix material and second substrate to provide at least one separator element including a continuous passage through a nanoscale hole and aperture.

16. The method of claim 15 further including the step of separating the matrix material into a plurality of tiles after the local droplet etching and wherein the tiles are separately attached to the second substrate.

17. The method of claim 15 wherein the matrix material is adhered to the second substrate by Van-der-Waals forces.

18. The method of claim 15 wherein including the step of coating the nanoscale hole with a semiconductor material different from a material of the walls of the nanoscale hole.

19. The method of claim 15 wherein the metal is selected from indium and gallium.

20. The method of claim 15 wherein the matrix material is gallium arsenide.

* * * * *